United States Patent [19]

Pelletier et al.

[11] Patent Number: 4,920,227

[45] Date of Patent: Apr. 24, 1990

[54] BENZOBICYCLIC CARBOXAMIDE 5-HT3 ANTAGONISTS

[75] Inventors: Jeffrey C. Pelletier, Lansdale, Pa.; Raymond D. Youssefyeh, Princeton Junction, N.J.; Henry F. Campbell, North Wales, Pa.

[73] Assignee: Rorer Pharmaceutical Corp., Fort Washington, Pa.

[21] Appl. No.: 277,611

[22] Filed: Nov. 29, 1988

[51] Int. Cl.$^5$ .................. C07D 451/02; C07D 211/60; C07D 143/78; C07D 149/41

[52] U.S. Cl. ..................... 546/133; 546/124; 546/127; 546/189; 564/89; 564/162; 564/163

[58] Field of Search ................. 546/133, 163, 162, 89, 546/189, 124, 127

[56] References Cited

U.S. PATENT DOCUMENTS 3,822,310  7/1974  Shen et al. ................. 564/162

OTHER PUBLICATIONS

The Merck Manual (Merck and Co., Rahway, N.J., 1979) pp. 1867 to 1869.

*Primary Examiner*—Mukund J. Shah
*Assistant Examiner*—E. C. Ward
*Attorney, Agent, or Firm*—James A. Nicholson; Martin Savitzky; Irme Jim Balogh

[57] ABSTRACT

Certain specific substituted benzobicyclic carboxamides and their valuable use as 5-HT3 antagonists having CNS and gastric prokenetic activity void of any significant $D_2$ receptor binding activity are disclosed.

8 Claims, No Drawings

BENZOBICYCLIC CARBOXAMIDE 5-HT3 ANTAGONISTS

FIELD OF THE INVENTION

This invention relates to benzobicyclic substituted carboxamide compounds which exhibit 5-HT$_3$ antagonist properties including CNS, anti-emetic and gastric prokinetic activity and which are void of any significant D$_2$ receptor binding affinity. This invention also relates to pharmaceutical compositions and methods for the treatment of gastrointestinal and mental disorders using said compounds.

5-Hydroxytryptamine, abbreviated "5-HT", is commonly known as serotonin. Serotonin is found throughout the body including the gastrointestinal tract, platelets, spleen and brain, appears to be involved in a great number of physiological processes such as neurotransmission at certain neurones in the brain, and is implicated in a number of central nervous system (CNS) disorders. Additionally, serotonin appears to act as a local hormone in the periphery; it is released in the gastrointestinal tract, where it increases small intestinal motility, inhibits stomach and colon motility, and stimulates stomach acid production. Serotonin is most likely involved in normal intestinal peristalsis.

The various physiological activities exerted by serotonin are related to the variety of different receptors found on the surface membrane of cells in different body tissue. The first classification of serotonin receptors included two pharmacologically distinct receptors discovered in the guinea pig ileum. The "D" receptor mediates smooth muscle contraction and the "M" receptor involves the depolarization of cholinergic nerves and release of acetylcholine. Three different groups of serotonin receptors have been identified and the following assignment of receptors has been proposed: D-receptors are 5-HT$_2$-receptors; M-receptors are termed 5-HT$_3$-receptors; and all other receptors, which are clearly not 5-HT$_2$ or 5-HT$_3$, should be referred to as 5-HT$_1$-like.

5-HT$_3$-receptors have been located in non-neurological tissue, brain tissue, and a number of peripheral tissues related to different responses. It has been reported that 5-HT$_3$-receptors are located on peripheral neurones where they are related to serotonin's (excitatory) depolarizing action. The following subtypes f 5-HT$_3$ receptor activity have been reported: action involving postganglionic sympathetic and parasympathetic neurones, leading to depolarization and release of noradrenaline and acetylcholine, respectively (5-HT$_{3B}$ subtype); action on enteric neurones, were serotonin may modulate the level of acetylcholine (5-HT$_{3C}$ subtype); and action on sensory nerves such as those involved in the stimulation of heart nerve endings to produce a reflex bradycardia (5-HT$_{3A}$ subtype), and also in the perception of pain.

Highly selective 5-HT$_3$-antagonists have been shown to be very effective at controlling and preventing emesis (vomiting) induced by chemotherapy and radiotherapy in cancer patients. The anti-emetic effects of 5-HT$_3$-antagonists in animals exposed to cancer chemotherapy or radiation are similar to those seen following abdominal vagotomy. The antagonist compounds are believed to act by blocking 5-HT$_3$-receptors situated on the cell membranes of the tissue forming the vagal afferent input to the emetic coordinating areas on the brain stem.

Serotonin is also believed to be involved in the disorder known as migraine headache. Serotonin released locally within the blood vessels of the head is believed to interact with elements of the perivascular neural plexus of which the afferent, substance P-containing fibers of the trigeminal system are believed relevant to the condition. By activating specific sites on sensory neuronal terminals, serotonin is believed to generate pain directly and also indirectly by enhancing the nociceptive effects of other inflammatory mediators, for example bradykinin. A further consequence of stimulating the afferent neurones would be the local release of substance P and possibly other sensory mediators, either directly or through an axon reflex mechanism, thus providing a further contribution to the vascular changes and pain of migraine. Serotonin is known to cause pain when applied to the exposed blister base or after an intradermal injection; and it also greatly enhances the pain response to bradykinin. In both cases, the pain message is believed to involve specific 5-HT$_3$ receptors on the primary afferent neurones.

5-HT$_3$-antagonists are also reported to exert potential antipsychotic effects, and are believed to be involved in anxiety. Although not understood well, the effect is believed to be related to the indirect blocking of serotonin 5-HT$_3$-mediated modulation of dopamine activity.

Many workers are investigating various compounds having 5-HT$_3$-antagonist activity.

REPORTED DEVELOPMENTS

The development of 5-HT$_3$ agents originated from work carried out with metoclopramide (Beecham's Maxolon, A. H. Robins' Reglan), which is marketed for use in the treatment of nausea and vomiting at high doses. Metoclopramide is a dopamine antagonist with weak 5-HT$_3$-antagonist activity, which becomes more prominent at higher doses. It is reported that the 5-HT$_3$ activity and not the dopamine antagonism is primarily responsible for its anti-emetic properties. Other workers are investigating this compound in connection with the pain and vomiting accompanying migraine.

Merrell Dow's compound MDL-72222 is reported to be effective as an acute therapy for migraine, but toxicity problems have reportedly ended work on this compound. Currently four compounds, A. H. Robin' Zacopride, Beecham's BRL-43694, Glaxo's GR-38032F and Sandoz' ICS-205-930 are in clinical trials for use in chemotherapy-induced nausea and vomiting. GR-38032F is also in clinica trials in anxiety and schizophrenia, and reportedly, Zacopride in anxiety, while ICS-205-930 has been shown to be useful in treating carcinoid syndrome.

Compounds reported as gastroprokinetic agents include Beecham's BRL-24924, which is a serotonin-active agent for use in gut motility disorders such as gastric paresis, audition reflux esophagitis, and is know to have also 5-HT$_3$-antagonist activity.

Metoclopramide, Zacopride, Cisapride and BRL-24924 are characterized by a carboxamide moiety situated para to the amino group of 2-chloro-4-methoxy aniline. BRL-43694, ICS-205930, GR-38032F and GR-65630 are characterized by a carbonyl group in the 3-position of indole or N-methyl indole. MDL-72222 is a bridged azabicyclic 3,5-dichlorobenzoate, while Zacopride, BRL-24924, BRL-43694 and ICS-205930 have also bridged azabicyclic groups in the form of a carboxamide or carboxylic ester.

Bicyclic oxygen containing carboxamide compounds wherein the carboxamide is ortho to the cyclic oxygen moiety are reported to have antiemetic and antipsychotic properties in EPO Publ. No. 0234872.

Dibenzofurancarboxamides and 2-carboxamide-substituted benzoxepines are reported to have 5HT$_3$-antagonist and gastroprokinetic activity in copending application Ser. Nos. 152,112, 152,192, and 168,824, all of which are assigned to the same assignee as the present application.

SUMMARY OF THE INVENTION

This invention relates to benzobicyclic carboxamide compounds having 5-HT$_3$ antagonist activity. Preferred compounds of this invention are of the formula

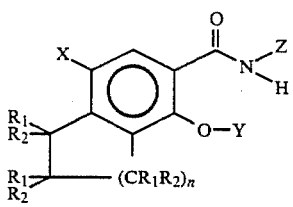

wherein:
X is hydrogen, alkyl, alkoxy, hydroxy, amino, mono- and di-alkylamino, halo, trifluoromethyl, nitro, sulfamyl, mono- and di-alkylsulfamyl, alkylsulfonyl, carboxy, carbalkoxy, carbamyl or mono- and di-alkylcarbamyl;
Y is hydrogen, alkyl, alkenyl, aralkyl,

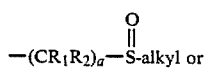

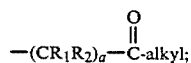

Z is

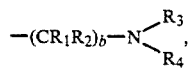

3-quinuclidine, 4-quinuclidine, 4-(1-azabicyclo[3.3.1]nonane), 3-(9-methylazabicyclo[3.3.1]nonane), 7-(3-oxo-9-methylazabicyclo[3.3.1]nonane) or 4-[3-methoxy-1-(3-[4-fluorophenoxy]propyl) piperidine];
$R_1$, $R_2$, $R_3$ and $R_4$ are independently hydrogen or alkyl;
vicinal $R_2$ groups may together form a carbocyclic ring;
vicinal $R_1$ rous may form a double bond;
a and b are 1 to 4;
n is 1 to 3;
and pharmaceutically acceptable salts thereof.

This invention related also to pharmaceutical compositions including an effective therapeutic amount of the aforementioned benzobicyclic carboxamide compound and therapeutic methods for the treatment of a patient suffering from gastrointestinal and/or psychochemical imbalances in the brain by administering said pharmaceutical composition.

Another aspect of the present invention relates to a process for the preparation of the above-described compounds.

DETAILED DESCRIPTION

As employed above and throughout the disclosure, the following terms, unless otherwise indicated, shall be understood to have the following meanings:

"Alkyl" means a saturated aliphatic hydrocarbon which may be either straight or branched-chained containing from about 1 to about 6 carbon atoms.

"Lower alkyl" means an alkyl group as above, having 1 to about 4 carbon atoms.

"Aralkyl" means an alkyl group substituted by an aryl radical were aryl means a phenyl or phenyl substituted with one or more substituents which may be alkyl, alkoxy, amino, nitro, carboxy, carboalkoxy, cyano, alkyl amino, halo, hydroxy, hydroxyalkyl, mercaptyl, alkyl mercaptyl, carboalkyl or carbamoyl. The preferred aralkyl groups are benzyl or phenethyl.

"Carbamyl" means a group of the formula

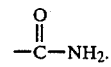

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Acyl" means an organic radical derived from an organic acid, a carboxylic acid, by the removal of its acid hydroxyl group. Preferred acyl groups are benzoyl and lower alkyl carboxylic acids groups such as acetyl and propionyl.

The chemical structures for the Z groups defined above are presented below.

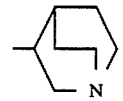 3-quinuclidine

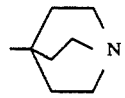 4-quinuclidine

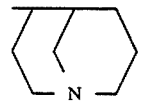 4-(1-azabicyclo[3.3.1]nonane)

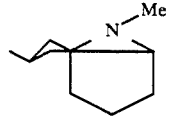 3-(9-methylazabicyclo[3.3.1]-nonane)

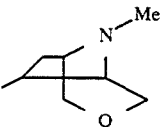 7-(3-oxo-9-methylazabicyclo[3.3.1]nonane)

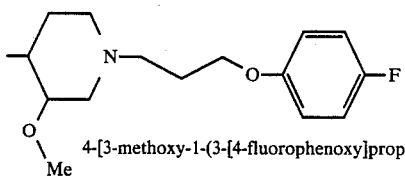
4-[3-methoxy-1-(3-[4-fluorophenoxy]propyl)piperidine]

Certain of the compounds of the present invention may exist in enolic or tautomeric forms, and all of these forms are considered to be included within the scope of this invention.

The compounds of this invention may be useful in the form of the free base, in the form of salts and as a hydrate. All forms are within the scope of the invention. Acid addition salts may be formed and are simply a more convenient form for use; and in practive, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitriated by side effects ascribable to the anions. Although pharmaceutically acceptable salts of said basic compound are preferred, all acid addition salts are useful as sources of the free base form even if the particular salt per se is desired only as an intermediate produce as, for example, when the salt is formed only for purposed of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexysulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

A preferred class of compounds is described by Formula I:

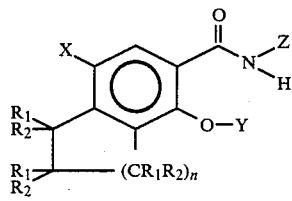

where:
X is hydrogen, hydroxy, amino, mono- and di-loweralkylamino, halo, trifluoromethyl, sulfamyl, mono- and di-loweralkylsulfamyl or loweralkylsulfonyl;
Y is loweralkyl,

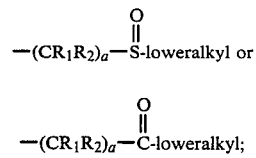

Z is

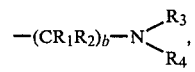

3-quinuclidine; 4-quinuclidine, 4-(1-azabicyclo[3.3.1]nonane), 3-(9-methylazabicyclo[3.3.1]nonane), 7-(3-oxo-9-methylazabicyclo[3.3.1]nonane) or 4-[3-methoxy-1-[4-fluorophenoxy]propyl) piperidine];
$R_1$, $R_2$, $R_3$ and $R_4$ are independently hydrogen or loweralkyl;
vicinal $R_2$ groups may together form a 5- to 7-member carbocyclic ring;
vicinal $R_1$ groups may form a double bond;
a and b are 1 to 3;
n is 1 to 3;
and pharmaceutically acceptable salts thereof.

More preferred compounds are those of Formula I where:
X is hydrogen or halo;
Y is methyl, ethyl, propyl, i-propyl, butyl, i-butyl, sec-butyl, t-butyl, pentyl,

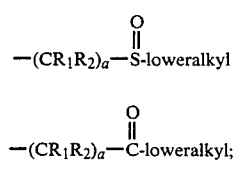

Z is 3-quinuclidine, 4-quinuclidine, 4-(1-azabicyclo[3.3.1]-nonane), 3-(9-methylazabicyclo[3.3.1]-nonane), 7-(3-oxo-9-methylazabicyclo[3.3.1]nonane) or 4-[3-methoxy-1-(3-[4-fluorophenoxy]propyl) piperidine];
$R_1$ and $R_2$ are independently hydrogen, methyl or ethyl;
vicinal $R_2$ groups may together form a 5- and 6-member carbocyclic ring;
vicinal $R_1$ groups may form a double bond;
a is 1 to 3;
n is 1 or 2;
and pharmaceutically acceptable salts thereof.

The most preferred compounds are those of Formula II:

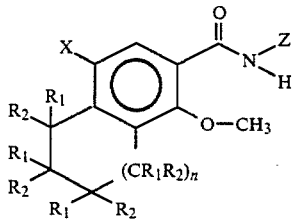

where:
X is chloro or bromo;
Z is 3-quinuclidine, 4-quinuclidine or 4-(1-azabicylco[3.3.1]nonane);
$R_1$ and $R_2$ are independently hydrogen, methyl or ethyl;
vicinal $R_2$ groups may together form a 5- or 6-member carbocyclic ring;
vicinal $R_1$ groups may form a double bond;
and pharmaceutically acceptable salts thereof.

Compounds of this invention may be prepared by the reaction of an amine of the formula $H_2N-Z$ with a suitably substituted carboxylic acid, acid halide or carboxylic ester of the indene, napthalane, 7(H)-cycloheptabenzene compounds, and dihydro or tetrahydro forms thereof, which correspond to the carboxamide of Formula I.

The carboxylic acid starting compounds and derivatives thereof for the above-mentioned reaction are also novel compounds and comprise part of the present invention. These materials comprise the appropriately substituted indene, indan, napthalene, 1,4-dihydronapthalene, tetralin, 7(H)-cycloheptabenzene, 5,6-dihydro-7(H)-cycloheptabenzene and 5,6,8,9-tetrahydro-7(H)-cycloheptabenzene carboxylic compounds correspondng to the appropriate carboxamide compounds of Formula I.

The carboxylic acid intermediate compounds may be prepared from starting materials such as 4-methoxyindene, 4-methoxyindan, 1-methoxynapthalene, 5-methoxy-1,4-dihydronapthalene, 5-methoxytetralin, 1-methoxy-7(H)-cycloheptabenzene, 1-methoxy-5,6-dihydro-7(H)-cycloheptabenzene or 1-methoxy-5,6,8,9-tetrahydro-7(H)-cycloheptabenzene. These starting materials are commercially available or may be prepared by known methods.

Halogenation of the position para to the ether of the starting material, preferably chlorination with preferred reagents such as N-chloro-succinimide and DMF, affords the methoxy-halo intermediate compound. Further halogenation in the ortho position, preferably bromination with N-bromosuccinimide and DMF, is followed by transformation of the ortho-halo substituent to a carboxy group, preferably by treatment with a strong base such as N-butyllithium and carbon dioxide. The carboxy compound is then reacted with an amine of the formula $H_{2;l}$ N-Z as defined above to prepare the compounds within the scope of Formula I. The reaction may be conducted at temperatures on the order of 0° C. using a catalytic amount of ethyl chloroformate in chloroform in the presence of triethylamine. The chloroformate adduct is reacted with the amine of the formula $H_2N-Z$ to obtain the desired carboxamide. The reaction may also be conducted in the presence of a dehydrating catalyst such as a carbodiimide in a solvent at room temperature.

Compounds including various X substituents may be prepared by suitable choice of starting material. Those substituents which require protection may protected and deprotected as necessary or may be converted into the desired substituent from an appropriate precursor group. For example, compounds where X is chloro, bromo or iodo, may be reacted with cuprous cyanide in quinoline at about 150° C. to produce compounds where X is cyano. Thè cyano group may be converted to the acids, esters or amides.

The halo group may also be converted to the $CF_3$ group by reaction with trifluoromethyliodide and copper powder at about 150° C. in DMF. The halo group may also be converted to the methylsulfonyl substituent by reaction with cuprous methanesulfinate in quinoline at 150° C.

When X is nitro, selective hydrogenation results in the corresponding amine, which may be mono- or dialkylated with loweralkyl halides or sulfates. The amino group may also be diazotized to the diazonium fluoride which is then thermally decomposed to the fluorine derivative compound. The amine may also be diazotized and heated in an aqueous medium to form the alcohol or heated in an alcohol to form the alkoxy compound. Chlorosulfonation of the amine group may form the corresponding sulfamyl or mono- and di-alkylsulfamyl groups.

Depending on the chemistry involved in the synthesis, these reactions may be carried out at any appropriate stage of the synthesis. For example, the synthesis of X starting from $NO_2$ may be done after the closed ring molecule or even after the carboxamide is prepared.

The compounds of this invention may contain at least one asymmetric carbon atom and may have two centers when $R_1=R_2$. As a result, the compounds of Formula I may be obtained either as racemic mixtures or as individual enantiomers. When two asymmetric centers are present the product may exist as a mixture of two diasteromers. The product may be synthesized as a mixture of the isomers and the desired isomer separated by conventional techniques such as chromatography or fractional crystalization from which each diasteromer may be resolved. On the other hand, synthesis may be carried out by known sterospecific processes using the desired form of the inermediate which would result in obtaining the desired specificity.

It is convenient to carry out condensation of the intermediate carboxylic acids mentioned above with the amines of the formula $H_2N-Z$ using the sterospecific materials. Accordingly, the acid may be resolved into its stereoisomers prior to condensation with resolved amine.

The compounds of this invention may be prepared by the following representative example.

EXAMPLE

The Preparation of (N1-Azabicyclo[2.2.2]oct-3-yl)-8-chloro-5-methoxytetralin-6-carboxamide Step 1. 5-Methoxytetralin Tin (II) chloride (0.2 mole) is added to a solution of 5-methoxy-tetralone (0.1 mole) in ethanol-conc. HCl (150 ml, 9:1) at reflux, and the reaction mixture is refluxed for 16 hours, cooled and the alcohol is evaporated. The aqueous residue is diluted with $H_2O$, extracted with ether, dried ($MgSO_4$) and evaporated to the desired product.

Step 2. 8-Chloro-5-methoxytetralin

N-Chlorosuccinimide (0.05 mole) is added all at once to the methoxytetralin of step 1 above (0.5 mole) in DMF (150 ml), stirred for 4 hours at 0° C. and poured into ice water. The precipitate is filtered, dried and used as is in the next step.

Step 3. 6-Bromo-8-chloro-5-methoxytetralin

N-Bromosuccinimide (0.028 mole) is added all at once to the chloromethoxytetralin of step 2 above (0.025 mole) in DMF (150 ml) at 0° C., stirred for 4 hours and poured into ice water. The precipitate is filtered, dried and used as is in the next step.

Step 4. 8-Chloro-5-methoxytetralin-6-carboxylic acid

N-Butyllithium (0.011 mole, hexane) is added dropwise to the bromochloromethoxytetralin of step 3 above (0.01 mole) in dry THF (100 ml) at −78° C. The reaction mixture is bubbled with $CO_2$ gas for 5 hours, warmed to 20° C. and poured into 10% aqueous HCl. The precipitate is filtered, dried and used as is in the next step.

Step 5. (N-1-Azabicyclo[2.2.2]oct-3yl)-8-chloro-5-methoxytetralin-6-carboxamide

Ethylchloroformate (4.9 mmoles) is added all at once to the tetralin carboxylic acid of step 4 above (5 mmoles) in chloroform (100 ml) and triethylamine (15 mmoles) at −23° C. and stirred for 1 hour. Aminoquinuclidine dihydrochloride (25 mmoles) and aqueous $K_2CO_3$ (25 ml, sat'd) are added to the reaction mixture which is stirred for 1 hour, diluted with $H_2O$ and separated. The organic layer is washed with $H_2O$, dried ($MgSO_4$) and evaporated affording the desired product.

The following compounds are prepared by procedures analogous to those described above.

(N-1-Azabicyclo[2.2.2]oct-3-yl)-7-chloro-4-methoxyindan-5-carboxamide.

(N-1-Azabicyclo[2.2.2]oct-3-yl)-4-chloro-1-methoxy-5,6,8,9-tetrahydro-7(H)-cycloheptabenzene-2-carboxamide.

(1-Azabicyclo[3.3.1]non-3-yl)-8-chloro-5-methoxytetralin-6-carboxamide.

(1-Azabicyclo[3.3.1]non-4-yl)-7-chloro-4-methoxyindan-5-carboxamide.

(1-Azabicyclo[3.3.1]non-4-yl)-4-chloro-1-methoxy-5,6,8,9-tetrahydro-7(H)-cycloheptabenzene-2-carboxamide.

Compounds within the scope of this invention have gastric prokinetic, anti-emetic and lack $D_2$ receptor binding activity and as such possess therapeutic value in the treatment of upper bowel motility and gastroesophageal reflux disorders. Further, the compounds of this invention may be useful in the treatment of disorders related to impaired gastrointestinal motility such as retarded gastric emptying, dyspepsia, flatulence, oesophageal reflux, peptic ulcer and emesis. Compounds of this invention exhibit 5-$HT_3$ antagonism and are considered to be useful in the treatment of psychotic disorders such as schizophrenia and anxiety and in the prophylaxis treatment of migraine and cluster headaches. These compounds are selective in that they have little or no dopaminergic antagonist activity.

Various tests in animals can be carried out to show the ability of the compounds of this invention to exhibit pharmacological responses that can be correlated with activity in humans. These tests involve such factors as the effect of the compounds of Formula I on gatric motility, emesis, selective antagonism of 5-$HT_3$ receptors and their $D_2$ dopamine receptor binding properties.

One such tst is the "Rat Gastric Emptying: Amberlite Bead Method". This test is carried out as follows:

The study is designed to assess the effects of a test agent on gastric emptying of a solid meal in the rat. The procedure is a modification of those used in L. E. Borella and W. Lippmann (1980) *Digestion* 20: 26–49.

PROCEDURE

Amberlite beads are placed in a phenol red solution and allowed to soak for several hours. Phenol red serves as an indicator, changing the beads from yellow to purple as their environment becomes more basic. After soaking, the beads are rinsed with 0.1 NaOH to make them purple and then washed with deionized water to wash away the NaOH.

The beads are filtered several times through 1.18 and 1.4 mm sieves to obtain beads with diameters in between these sizes. This is done using large quantities of deionized water. The beads are stored in saline until ready to use.

Male Sprague-Dawley rats are fasted 24 hours prior to the study with water ad libitum. Rats are randomly divided in treatment groups with an N of 6 or 7.

Test agents are prepared in 0.5% methylcellulose and administered to the rats orally in a 10 ml/kg dose volume. Control rats receive 0.5% methylcellulose, 10 ml/kg p.o. One hour after dosing, rats are given 60 Amberlite beads intra-gastrically. The beads are delivered via a 3 inch piece of PE 205 tubing attached to a 16 gauge tubing placed inside the tubing adapter to preent the beads from being pulled back into the syringe. The beads are flushed into each rat's stomach with 1 ml saline.

Rats are sacrificed 30 minutes after receiving the beads and their stomachs are removed. The number of beads remaining in each stomach is counted after rinsing the beads with NaOH.

The number of beads remaining in each stomach is subtracted from 60 to obtain the number of beads emptied. The mean number of beads ± S.E.M. is determined for each treatment group. The percent change from control is calculated as follows:

$$\frac{\text{Mean Control Group} - \text{Mean Test Agent Group}}{\text{Mean Control Group}} \times 100$$

Statistical significance may be determined using a t-test for independent samples with a probability of 0.05 or less considered to e significant.

In order to demonstrate the ability of the compounds of this invention as anti-emetic agents the following test for "Cisplatin-Induced Emesis in the Ferret" may be used. This test is a modified version of a paper reported by A. P. Florezyk, J. E. Schurig and W. T. Brodner in *Cancer Treatment Reports:* Vol. 66, No. 1. January 1982.

Cisplatin had been shown to cause emesis in the dog and cat. Florczyk, et al. have used the ferret to demonstrate the same effects.

PROCEDURE

Male castrated, Fitch ferrets, weighing between 1.0 and 1.5 kg have an in Indwelling catheter placed in the jugular vein. After a 2–3 day recovery period, the experimental procedure is begun.

30 minutes prior to administration of Cisplatin, ferrets are dosed with the compound in 0.9% saine (i.v.) at a dose volume of 2.0 ml/kg.

45 minutes after administration of Cisplatin, ferrets are again dosed with 0.9% saline (i.v.) mixture at a dose volume of 2.0 ml/kg.

Cisplatin is administered (i.v.) 30 minutes after the first dosing with the 0.9% saline. Cisplatin, 10 mg/kg is administered in a dose volume of 2.0 ml/kg.

The time of Cisplatin administration is taken as time zero. Ferrets are observed for the duration of the experiment (4 hours). The elapsed time to the first emetic episode is noted and recorded, as are the total number of periods of emesis.

An emetic (vomiting) episode is characterized by agitated behavior, such as pacing around the cage and rapid to and fro movements. Concurrent with this behavior are several retching movements in a row, followed by a single, large, retch which may or may not expulse gastric contents. Immediately following the single large retch, the ferret relaxes. Single coughs or retches are not counted as vomiting episodes.

D-2 Dopamine Receptor Binding Assay

The D-2 dopamine receptor binding assay has been developed with slight modifications using the method of Ian Cresse, Robert Schneider and Solomon H. Snyder, *Europ. J. Pharmacol.* 46: 377–381 (1977). Spiroperidol is a butyrophenone neuroleptic whose affinity for dopamine receptors in brain tissue is greater than that of any other known drug. It is a highly specific D-1 dopamine (non-cyclase linked) receptor agent with $K_i$ values of 0.1–0.5 for D-2 inhibition and 300 nM for D-1 inhibition.

Sodium ions are important regulators of dopamine receptors. The affinity of the D-2 receptor is markedly enhanced by the presence of millimolar concentrations of sodium chloride. The Kd in the absence and presence of 120 mM sodium chloride is 1.2 and o.086 nM respectively. Sodium chloride (120 mM) is included in all assays as a standard condition.

The caudate nucleum (corpous striatum) is used as the receptor source because it contained the highest density of dopamine receptors in the brain and periphery.

PROCEDURE

Male Charles-River rats weighing 250–300 g are decapitated and their brains removed, cooled on ice, and caudate dissected immediately and frozen on dry ice. Tissue can be stored indefinitely at −70° C. For assay caudate is homogenized in 30 ml of tris buffer (pH 7.7 at 25° C.) using the polytron homogenizer. The homogenate is centrifuged at 40,000 g (18,000–19,000 RPM in SS-34 rotor) for 15 minutes. Pellet is resuspended in fresh buffer and centrifuged again. The final pellet is resuspended in 150 volumes of assay buffer.

Specific $^3$H-spiroperiodol binding is assayed in a total 2 ml reaction volume consisting of 500 μl of caudate homogenate, 50 mM tris buffer (pH 7.4 at 35° C.), 5 mM MgSO$_4$, 2 mM EDTA 2NA, 120 mM NaCl, 0.1% ascorbic acid, 0.4 nM $^3$H-spiroperidol and test compound or assay buffer. When catecholamines are included in the assay, 10 μM pargyline should be included in the reaction mixture to inhibit monoamine oxidase. Samples are incubated at 35° C. for 30 minutes followed by addition of 5 ml ice cold 50 mM TRIS (pH 7.7 at 25° C.) and filtration through GF/B glass fiber filters on a Brandel Receptor Binding Filtration apparatus. Filters are washed twice with an additional 5 ml of tris buffer each. Assay groups are performed in triplicate and 1 μM D(+) butaclamol is used to determine nonspecific binding. Filters are placed in vials containing 10 ml of Ecoscint phosphor, shaken for 30 minutes and dpm determined by liquid scintillation spectrophotometry using a quench curve. Proteins are determined by the method of Bradford, M. Anal. Biochem 72, 248(1976) using Bio-Rad's coomassie blue G-250 dye reagent. Bovine gamma Globulin supplied by BIO-RAD is used as the protein standard.

BEZOLD-JARISCH EFFECT IN ANESTHETIZED RATS

Male rats 260–290 g are anesthetized with urethane 1.25 g/kg$^{-1}$ i.p., and the trachea cannulated. The jugular vein is cannulated for intravenous (i.v.) injection of drugs. Blood pressure is recorded from a cannula in the left carotid artery and connected to a heparin/saline-filled pressure transducer. Continuous heart rate measurements are taken from the blood pressure recordings. The Bezold-Jarisch effect is evoked by rapid, bolus i.v. injections of 5-HT and measurements are made of the fall in heart rate. In each rate, consistent responses are first established with the minimum dose of 5-HT that evokes a clear fall in heart rate. Injections of 5-HT are given every 12 minutes and a dose-response curve for the test compound is established by injecting increasing doses of compound 5 minutes before each injectin of 5-HT. The effect of the compound on the 5-HT-evoked bradycardia is calculated as a percent of the bradycardia evoked by 5-HT before injection of compound.

In separate experiments to measure the duration of 5-HT antagonism caused by the compounds of this invention, a single dose of compound is injected 5 minutes before 5-HT, and the effects of 7 repeated challenges with 5-HT are then monitored. The effects of the compound on the efferent vagal limb of the Bezold-Jarisch reflex are checked by electrically stimulating the peripheral end of a cut vagus nerve. Unipolar electrical stimulation is applied every 5 minutes via a pair of silver electrodes, using 1 ms rectangular pulses in 5 strains with a maximally-effective voltage (20 V at 10 Hz). Pulse frequency may vary from 5–30 Hz and frequency-response curves are constructed before and 10 minutes after i.v. injection of a single dose of compound.

The results of these above tests indicate that the compounds for this invention exhibit a valuable balance between the peripheral and central action of the nervous system and may be useful in the treatment of disorders related to impaired gastro-intestinal motility such as gastric emptying, dyspepsia, flatulence, esophageal reflux and peptic ulcer and in the tretment of disorders of the central nervous system such as psychosis.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, opthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose of saccharin may be added or a flavoring agent such as peppermint, oil of wintergreen, or cherry flavoring. When the dosage unit form is a capsule it may contain, in addition to materials of the above type, a liquid carrier. Various other materials may be present as coatings or to otherwise modify thephysical form of the dosage unit. For instance, tablets, pills, or capsules may be coated with shellac, sugar or both. A syrup or elixir may contain the active compound sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperiotoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storge and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride.

Prolonged absorption of the injectable compositions involves the incorporation of an agent delaying absorption, for xample, aluminum monostearate and gelatin.

Sterile injectable solutions are prepared by incorporating the active compound in the require amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparations are vacuum drying and the freeze drying technique which yield a powder of the active ingredient plus any additional desired ingredient from previously sterile-filtered solution thereof.

The therapeutic compounds of this invention may be administered alone to a mammal or in combination with pharmaceutically acceptable carriers, as noted above, the proportion of which is determined by the solutibility and chemical nature of the compound, chosen route of administration and standard pharmaceutical practice.

The physician will determine the dosage of the present therapeutic agents which will be most suitable for prophylaxis or treatment and will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 20 mg or from about 0.01 mg to about 5 mg/kg of body weight per day and higher although it may be administered in several different dosage units from once to several times a day. Higher dosages are required for oral administration.

We claim:

1. A compound of the formula

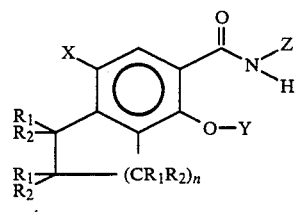

wherein:

X is hydrogen, hydroxy, amino, mono- and di-loweralkylamino, halo, trifluoromethyl, sulfamyl, mono- and di-loweralkylsulfamyl or loweralkylsulfonyl;

Y is loweralkyl,

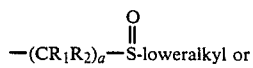

or

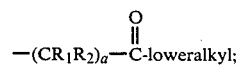

Z is

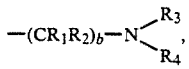

3-quinuclidine, 4-quinuclidine, 4-(1-azabicyclo [3.3.1]nonane), 3-(9-methylazabicyclo[3.3.1]nonane), 7-(3-oxo-9-methylazabicyclo[3.3.1]nonane) or 4-[3-methoxy-1-(3-[4-fluorophenoxy]propyl)piperidine];

$R_1$, $R_2$, $R_3$ and $R_4$ are independently hydrogen or loweralkyl;

vicinal $R_2$ groups may together form a 5- to 7-member carbocyclic ring;

vicinal $R_1$ groups may form a double bond;

a and b are 1 to 3;

n is 1 to 3;

or a pharmaceutically acceptable salt thereof.

2. The compound of claim 1 wherein:

X is hydrogen or halo;

Y is methyl, ethyl, propyl, i-propyl, butyl, i-butyl, sec-butyl, t-butyl, pentyl,

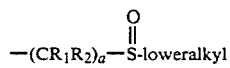

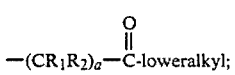

Z is 3-quinuclidine, 4-quinuclidine, 4-(1-azabicyclo[3.3.1]-nonane), 3-(9-methylazabicyclo[3.3.1]-nonane), 7-(3-oxo-9-methylazabicyclo[3.3.1]nonane) or 4-[3-methoxy-1-(3-[4-fluorophenoxy]propyl) piperidine];

$R_1$ and $R_2$ are independently hydrogen, methyl or ethyl;

vicinal $R_2$ groups may together form a 5- or 6-member carbocyclic ring;

vicinal $R_1$ groups may form a double bond; a is 1 to 3; n is 1 or 2;

or a pharmaceutically acceptable salt thereof.

3. A compound of the formula

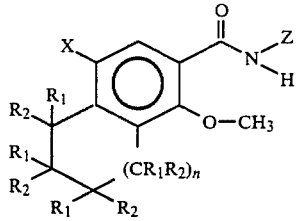

where:

X is chloro or bromo;

Z is 3-quinuclidine, 4-quinuclidine or 4-(1-azabicyclo[3.3.1]nonane);

$R_1$ and $R_2$ are independently hydrogen, methyl or ethyl;

vicinal $R_2$ groups may together form a 5- or 6-member carbocyclic ring;

vicinal $R_1$ groups may form a double bond; or a pharmaceutically acceptable salt thereof.

4. A compound according to claim 1 which is (N-1-azabicyclo[2.2.2]oct-3-yl)-8-chloro-5-methoxytetralin-6-carboxamide or a pharmaceutically acceptable salt thereof.

5. A compound according to claim 1 which is (N-1-azabicyclo[2.2.2]oct-3-yl)-7-chloro-4-methoxyindan-5-carboxamide or a pharmaceutically acceptable salt thereof.

6. A compound according to claim 1 which is (N-1-azabicyclo[2.2.2]oct-3-yl)-4-chloro-1-methoxy-5,6,8,9-tetrahydro-7(H)-cycloheptabenzene-2-carboxamide or a pharmaceutically acceptable salt thereof.

7. A compound according to claim 1 which is (1-azabicyclo[3.3.1]non-4-yl)-8-chloro-5-methoxytetralin-6-carboxamide or a pharmaceutically acceptable salt thereof.

8. A method for the treatment of a patient suffering from emesis comprising administering thereto an effective anti-emetic amount of a compound according to claim 1.

* * * * *